United States Patent [19]

Francis et al.

[11] 4,028,363

[45] June 7, 1977

[54] ISOQUINOLINE DERIVATIVES

[75] Inventors: Robert John Francis, Harpenden; John Glyn Allen, St. Albans, both of England

[73] Assignee: Hoffmann-La Roche Inc., Nutley, N.J.

[22] Filed: Mar. 3, 1976

[21] Appl. No.: 663,385

[52] U.S. Cl. .................. 260/286 R; 260/288 D; 424/232; 424/263
[51] Int. Cl.² .................................. C07D 217/24
[58] Field of Search ............... 260/288 D, 286 R

[56] References Cited

UNITED STATES PATENTS

| | | | |
|---|---|---|---|
| 3,291,799 | 12/1966 | Wenner | 260/288 D |
| 3,590,044 | 6/1971 | Den Hollander | 260/288 D |

*Primary Examiner*—R. Gallagher
*Attorney, Agent, or Firm*—Samuel L. Welt; George M. Gould; William G. Isgro

[57] ABSTRACT

2-Amidino-4-hydroxy-1,2,3,4-tetrahydroisoquinoline, prepared from 4-hydroxy-1,2,3,4-tetrahydroisoquinoline and a compound which yields the amidino group, as well as its salts, are described.

2 Claims, No Drawings

ISOQUINOLINE DERIVATIVES

BRIEF SUMMARY OF THE INVENTION

The invention relates to 2-amidino-4-hydroxy-1,2,3,4-tetrahydroisoquinoline and its pharmaceutically acceptable acid addition salts.

In another aspect, the invention relates to processes for preparing 2-amidino-4-hydroxy-1,2,3,4-tetrahydroisoquinoline and its acid addition salts.

DETAILED DESCRIPTION OF THE INVENTION

The isoquinoline derivative of the invention is the compound 2-amidino-4-hydroxy-1,2,3,4-tetrahydroisoquinoline characterized by the formula

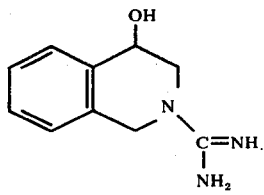

or a pharmaceutically acceptable acid addition salt thereof.

In accordance with the process provided by the present invention, the isoquinoline derivative of formula I and acid addition salts thereof, are prepared by reacting 4-hydroxy-1,2,3,4-tetrahydroisoquinoline characterized by the formula

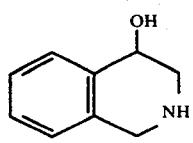

or a pharmaceutically acceptable acid addition salt thereof, with a compound which yields the amidino group and, if desired, converting the resulting compound, if an acid addition salt, into the free base or into a different acid addition salt or a pharmaceutically acceptable salt or, if the free base, into a pharmaceutically acceptable acid addition salt.

The 4-hydroxy-1,2,3,4-tetrahydroisoquinoline, i.e., the starting material of formula II, is known and can be prepared, for example, by reacting orthophthalaldehyde with nitromethane in the presence of anhydrous sodium carbonate and reducing the resulting 2-(1-hydroxy-2-nitroethyl)-benzaldehyde in the presence of platinum oxide.

In accordane with a preferred embodiment of the process of the invention, the amine of formula II is reacted with an acid addition salt of a urea derivative characterized by the formula

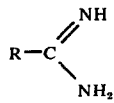

wherein R is alkylmercapto or alkoxy,
to give an acid addition salt of 2-amidino-4-hydroxy-1,2,3,4-tetrahydroisoquinoline of formula I.

The preferred acid addition salts of the urea derivatives of formula III are acid addition salts of S-(lower alkyl)-isothioureas or O-(lower alkyl)-pseudoureas. As used herein, the term "lower alkyl" is understood to mean straight-chain, as well as branched-chain alkyl, which preferably contain from 1 to 6 carbon atoms, for example, methyl, ethyl, propyl, isopropyl or the like.

The reaction of the amine of formula II with an acid addition salt of a urea derivative of formula III is preferably carried out in an inert solvent medium. As the solvent medium there can be used, for example, an aqueous medium or an aqueous medium containing a water-miscible organic solvent, for example, a lower alkanol such as methanol or ethanol. An aqueous medium is especially preferred. The temperature and pressure at which the reaction is carried out are not critical. Thus, the reaction can be carried out at room temperature or at a temperature above or below room temperature, and at atmospheric pressure or at a reduced or elevated pressure. When an acid addition salt of a S-(lower alkyl)-isothiourea is used, the reaction is advantageously carried out at a temperature in the range of from about 20° C. to 100° C., preferably in the range of from about 25° C. to 30° C., and at atmospheric pressure.

According to another process embodiment, the amine of formula II or an acid addition salt thereof is reacted with cyanamide. This reaction can be carried out in the presence or absence of a solvent. Thus, for example, the reaction can be carried out by fusing an acid addition salt of the amine with cyanamide. It is preferred, however, to carry out the reaction in a non-polar inert organic solvent, for example, an aromatic hydrocarbon such as toluene or xylene. When the reaction is carried out in an aromatic hydrocarbon, it is expedient to heat the reaction mixture; for example, at a temperature in the range of from about 100° C, up to the reflux temperature of the reaction mixture, preferably at the reflux temperature of the reaction mixture. The reaction with cyanamide can also be carried out in other solvents, for example, water, lower alkanol such as methanol, ethanol, or the like, or an aqueous lower alkanoic acid.

The conversion of an acid addition salt obtained into the free base or into a different acid addition salt can be carried out according to known procedures. Similarly, known procedures can be used for the conversion of the free base into an acid addition salt.

The 2-amidino-4-hydroxy-1,2,3,4-tetrahydroisoquinoline of formula I forms acid addition salts with inorganic and organic acids. The preferred acid addition salts are formed with pharmaceutically acceptable inorganic acids, for example, hydrochloric acid, hydrobromic acid, sulfuric acid, or the like, and with pharmaceutically acceptable organic acids, for example, methanesulfonic acid, ethanesulfonic acid, paratoluenesulfonic acid, benzenesulfonic acid, acetic acid, tartaric acid, maleic acid, malic acid, benzoic acid, salicylic acid, ascorbic acid, or the like.

The isoquinoline of formula I and its pharmaceutically acceptable acid addition salts, provided by the present invention, exhibit antihypertensive activity when administered, for example, intravenously to experimental mammals such as cats, and are therefore useful as antihypertensive agents.

The 2-amidino-4-hydroxy-1,2,3,4-tetrahydroisoquinoline of formula I and its pharmaceutically acceptable acid addition salts may be used as medicaments in the form of pharmaceutical preparations which contain them in association with a compatible pharmaceutical carrier. Such a carrier may be any organic or inorganic carrier compatible with the compound of formula I and suitable for enteral or parenteral administration, for example, water, gelatin, lactose, starch, magnesium stearate, vegetable oils, polyalkyleneglycols, or the like. The pharmaceutical preparations may be made up in a solid form, for example, as tablets, dragees, suppositories or capsules, or in a liquid form, for example, as solutions, suspensions or emulsions. The pharmaceutical preparations may be subjected to conventional pharmaceutical operations such as sterilization and may contain adjuvants such as wetting agents, preservatives, stabilizers, salts for adjustment of the osmotic pressure and buffers.

The daily dosage of 2-amidino-4-hydroxy-1,2,3,4-tetrahydroisoquinoline or a pharmaceutically acceptable acid addition salt thereof, which is to be administered to a warm-blooded animal, i.e., a mammal, may suitably be in the approximate range of from 25 mg. to 500 mg., preferably from 50 mg. to 250 mg. The daily dosage may be administered in one or in divided doses and may be increased or decreased according to the needs of the patient requiring treatment with the compound of formula I or a pharmaceutically acceptable acid addition salt thereof.

The Example which follows further illustrates the present invention. All temperatures are in degrees Centigrade, unless otherwise mentioned.

EXAMPLE

Preparation of 2-amidino-4-hydroxy-1,2,3,4-tetrahydroisoquinoline sulfate

A solution of 1.3 g. of S-methyl-isothiourea sulfate in 5 ml. of water at about 20° C. was added to 1.2 g. of 4-hydroxy-1,2,3,4-tetrahydroisoquinoline. The resulting mixture was maintained at about 25°–30° C. with occasional shaking. After a short time, methyl-mercaptan began to escape and, upon standing for 1–2 days, crystals formed. The crystals were removed by filtration and rinsed with ice-cold water and with ether. Recrystallization from water yielded 2-amidino-4-hydroxy-1,2,3,4-tetrahydroisoquinoline sulfate, having a melting point of 264°–266° C. (uncorrected).

We claim:

1. 2-Amidino-4-hydroxy-1,2,3,4-tetrahydroisoquinoline characterized by the formula

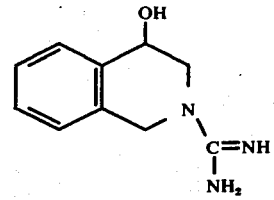

or a pharmaceutically acceptable acid addition salt thereof.

2. 2-Amidino-4-hydroxy-1,2,3,4-tetrahydroisoquinoline sulfate.

* * * * *

UNITED STATES PATENT AND TRADEMARK OFFICE
CERTIFICATE OF CORRECTION

PATENT NO. : 4,028,363
DATED : June 7, 1977
INVENTOR(S) : Robert John Francis et al.

It is certified that error appears in the above-identified patent and that said Letters Patent are hereby corrected as shown below:

Cover Sheet, after
"[21] Appl. No.: 663,385"     insert:

[30] Foreign Application Priority Data

March 13, 1975     England     10534/75

*Signed and Sealed this*

*Twenty-seventh* Day of *September 1977*

[SEAL]

Attest:

RUTH C. MASON
*Attesting Officer*

LUTRELLE F. PARKER
*Acting Commissioner of Patents and Trademarks*